(12) United States Patent
Johnson (10) Patent No.: US 11,266,426 B2
(45) Date of Patent: Mar. 8, 2022

(54) STREAMLINED TREATMENT OF CLOT REMOVAL, ANGIOPLASTY AND PREVENTION OF RESTENOSIS USING A SINGLE INTEGRATED INTRAVASCULAR DEVICE

(71) Applicant: DePuy Synthes Products, Inc., Raynham, MA (US)

(72) Inventor: Kirk Johnson, Weston, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 314 days.

(21) Appl. No.: 16/508,121

(22) Filed: Jul. 10, 2019

(65) Prior Publication Data

US 2021/0007761 A1    Jan. 14, 2021

(51) Int. Cl.
*A61B 17/22*   (2006.01)
*A61M 25/10*   (2013.01)
(Continued)

(52) U.S. Cl.
CPC ........ *A61B 17/22032* (2013.01); *A61F 2/958* (2013.01); *A61M 25/10184* (2013.11);
(Continued)

(58) Field of Classification Search
CPC .... A61B 17/22032; A61B 2017/22001; A61B 2017/22002; A61B 2017/22034; A61B 2017/22035; A61B 2017/22038; A61B 2017/22061; A61M 25/10184; A61F 2/95; A61F 2/958; A61F 2/962; A61F 2/966; A61F 2002/9528; A61F 2002/9583; A61F 2002/9665

See application file for complete search history.

(56) References Cited

U.S. PATENT DOCUMENTS 5,766,192 A    6/1998  Zacca
6,821,291 B2  11/2004  Bolea et al.
(Continued)

FOREIGN PATENT DOCUMENTS

WO    2011082319    7/2011
WO    2014087245    6/2014
WO    2017019572    2/2017

*Primary Examiner* — Robert A Lynch
(74) *Attorney, Agent, or Firm* — Cohen & Hildebrand, PLLC (57) ABSTRACT

A single integrated intravascular device including a stentriever and semi-compliant balloon housed therein. After traversing a clot, the device is deployed to a self-expanded state engaging the clot therein, whereupon the device along with the embedded clot is removed. Detecting through imaging a stenosis at an original position of the captured clot, the device is reintroduced to that location and the stentriever is deployed to a self-expanded state. Inflating the semi-compliant balloon enlarges the stentriever to a hyper-expanded state greater than the self-expanded state thereby dilating the vessel while simultaneously completely detaching/releasing the stentriever from a remaining portion of the device. Then the semi-compliant balloon is collapsed and withdrawn along with the remaining portion of the device, while the detachable/releasable portion of the stentriever in the self-expanded state remains in the vessel.

15 Claims, 9 Drawing Sheets

(51) Int. Cl.
*A61F 2/958* (2013.01)
*A61B 17/00* (2006.01)

(52) U.S. Cl.
CPC .......... *A61B 2017/00561* (2013.01); *A61B 2017/00862* (2013.01); *A61B 2017/22001* (2013.01); *A61B 2017/22002* (2013.01); *A61B 2017/22038* (2013.01); *A61B 2017/22061* (2013.01)

(56) References Cited

U.S. PATENT DOCUMENTS

| | | | |
|---|---|---|---|
| 6,986,778 B2 | 1/2006 | Zadno-Azizi |
| 7,258,696 B2 | 8/2007 | Rabkin et al. |
| 9,039,749 B2 | 5/2015 | Shrivastava et al. |
| 9,114,031 B2 | 8/2015 | Fulton, III |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Bures et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2002/0099405 A1* | 7/2002 | Yurek .................. A61F 2/966 606/198 |
| 2008/0046063 A1 | 2/2008 | Boatman et al. |
| 2010/0137892 A1 | 6/2010 | Krolik et al. |
| 2010/0305678 A1 | 12/2010 | Alaswad |
| 2011/0251674 A1* | 10/2011 | Schmid .................. A61F 2/90 623/1.16 |
| 2014/0343595 A1 | 11/2014 | Monstadt et al. |
| 2015/0313732 A1 | 11/2015 | Fulton, III |
| 2016/0166811 A1 | 6/2016 | Alaswad |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Fran et al. |
| 2017/0231646 A1 | 8/2017 | Epstein et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Fieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |

(56) References Cited

U.S. PATENT DOCUMENTS

| | | |
|---|---|---|
| 2017/0348014 A1 | 12/2017 | Wallace et al. |
| 2017/0348514 A1 | 12/2017 | Guyon et al. |
| 2019/0133747 A1 | 5/2019 | Janardhan et al. |

* cited by examiner

STREAMLINED TREATMENT OF CLOT REMOVAL, ANGIOPLASTY AND PREVENTION OF RESTENOSIS USING A SINGLE INTEGRATED INTRAVASCULAR DEVICE

BACKGROUND OF THE INVENTION

Field of the Invention

The present invention relates to an intravascular device. In particular, the present invention is directed to an improved single integrated intravascular device including a stentriever and balloon providing multifunctional treatment including clot removal, angioplasty and/or prevention of restenosis using a single device.

Description of Related Art

Mechanical thrombectomy devices (e.g., stent trievers or stentrievers) are commonly used to remove a clot, thrombus, occlusion or blockage that is occluding blood flow in an artery. Using standard imaging techniques (e.g., X-ray radiology), a guidewire alone may be advanced through an artery across and beyond a target clot, thrombus, occlusion or blockage followed thereafter by a microcatheter tracked over the guidewire. Alternatively, the microcatheter together with the guidewire disposed in the lumen of the microcatheter may be advanced simultaneously as a single unit through the artery across and beyond the target clot. In either case, with the microcatheter in position at the target site, the guidewire is proximally withdrawn and the mechanical thrombectomy device (e.g., stent retriever or stentriever) is advanced through the lumen of the microcatheter so that the stentriever crosses (traverses) the target clot. Now the microcatheter is proximally withdrawn unsheathing (i.e., freeing) the mechanical thrombectomy device coinciding with the occluding blockage. No longer radially constrained by the microcatheter, the mechanical thrombectomy device automatically radially self-expands to an enlarged maximum diameter. As the stentriever self-expands engaging the thrombus therein, it applies a radial force that compresses the thrombus against the vessel wall immediately restoring partial reperfusion of the distal vasculature. After passage of a predetermined period of time (e.g., approximately 2-5 minutes) the thrombus is sufficiently embedded in the spaces or openings between struts of the expanded stentriever. The microcatheter and mechanical thrombectomy device with the clot captured, embedded or engaged therein are simultaneously withdrawn as a single unit from the body.

Sometimes, an underlying stenosis (i.e., narrowing of the artery due to build-up of plaque) present behind the clot initially goes undetected, revealed to the interventionalist only after the thrombus itself has been removed. In such circumstance, to restore blood flow in the artery a separate angioplasty procedure is performed using a separate device, e.g., a balloon catheter. Once the catheter has been advanced to coincide with the narrowed opening of the vessel a balloon disposed on the end of the catheter is inflated. As the balloon expands, the plaque is pushed radially outward against the inner walls of the vessel thereby restoring blood flow therethrough. If necessary, in a third and separate procedure from that of the removal of the clot and opening of the narrowed vessel, a mesh stent separate from the stentriever and balloon catheter may be deployed and left permanently implanted in the body to maintain patency.

It is therefore desirable to develop a streamlined multifunctional treatment to carry out clot capture, angioplasty and/or prevention of restenosis using a single integrated intravascular device comprising a stentriever and semi-compliant balloon eliminating the need to perform separate medical procedures using separate devices.

SUMMARY OF THE INVENTION

An aspect of the present invention is directed to a streamlined multifunctional treatment to carry out clot capture, angioplasty and/or prevention of restenosis using a single integrated intravascular device comprising a self-expanding stentriever and semi-compliant balloon eliminating the need to perform separate medical procedures using separate devices.

Another aspect of the present invention relates to a single integrated intravascular device including a pusher member having a proximal end, an opposite distal end; and a self-expanding stentriever comprising an open scaffolding formed by multiple struts secured together. The self-expanding stentriever is transitionable upon withdraw of an externally applied mechanical force imposed by the microcatheter between a compressed state having a reduced diameter and a self-expanded state having an enlarged diameter. Proximal and distal ends of the self-expanding stentriever are secured to the pusher member at respective proximal and distal securement points, the self-expanding stentriever is detachable or releasable from the pusher member at the respective proximal and distal securement points. The device further including a semi-compliant balloon housed within the self-expanding stentriever and secured to the pusher member extending axially through the semi-compliant balloon; and an inflation lumen defined axially in the pusher member in fluid communication with the semi-compliant balloon.

While another aspect of the present invention is directed to a method for using a single integrated intravascular device as described in the preceding paragraph. The method including the step of advancing a guidewire and microcatheter into a vessel across a target clot. The guidewire is then proximally withdrawn while maintaining in position the microcatheter in the vessel traversing the target clot. While the self-expanding stentriever is in the compressed state with the semi-compliant balloon in a deflated state housed therein, the single integrated intravascular device is loaded into the lumen of the microcatheter. Then, the single integrated intravascular device is advanced through the lumen of the microcatheter using the pusher member so that the self-expanding stentriever coincides with the target clot. At this point the microcatheter is proximally withdrawn from the vessel, while the single integrated intravascular device is maintained within the vessel crossing the target clot. The self-expanding stentriever when unsheathed from the microcatheter automatically transitions to the self-expanded state engaging the target clot in the open scaffolding of the self-expanding stentriever, while the semi-compliant balloon housed within the self-expanding stentriever is maintained in a deflated state so as not to interfere with engagement and subsequent embedding of the target clot in the self-expanding stentriever.

Still another aspect of the present invention relates to a method for using a single integrated intravascular device including a stentriever and semi-compliant balloon housed within the stentriever. The single integrated intravascular device is first introduced into a vessel to traverse a target clot. Thereafter, the stentriever is deployed to a self-expanded state and the target clot is embedded therein. The single integrated intravascular device with the embedded clot therein is removed from the vessel. Through imaging, an underlying residual stenosis in the vessel is detected at an original position of the captured target clot. Whereupon, the single integrated intravascular device is reintroduced into the vessel to a location where the stentriever coincides with the detected underlying residual stenosis. Again, the stentriever is deployed so that it transitions from a compressed state to a self-expanded state. Next, the semi-compliant balloon is inflated with inflation media to enlarge the stentriever to a hyper-expanded state having a diameter larger than the self-expanded state thereby dilating the vessel at the location of the detected underlying residual stenosis while simultaneously completely detaching or releasing the stentriever from a remaining portion of the single integrated intravascular device. The semi-compliant balloon is now collapsed by purging the inflation media therefrom. Lastly, the remaining portion of the single integral intravascular device is proximally withdrawn from the vessel, while maintaining in position within the vessel at the position of the detected underlying residual stenosis the detachable or releasable portion of the stentriever in the self-expanded state.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which.

DETAILED DESCRIPTION OF THE INVENTION

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "clot", thrombus, or "blockage" are used interchangeably.

The present invention is directed to a single integrated intravascular device that includes a self-expanding stentriever and a semi-compliant balloon. The term "semi-compliant balloon" is herein defined as a balloon that distends approximately 10% of the diameter between the nominal pressure (pressure at labeled diameter) and the rated burst pressure (95% confidence that 99.9% will not fail at or below rated burst). Exemplary semi-compliant balloon materials include, but are not limited to, Polyethylene, Polyolefin Copolymer or Polyamide (Nylon). Heretofore, multiple intravascular treatments (clot removal; angioplasty; prevention of restenosis) were performed in succession, one following the other, each employing a different separate device dedicated exclusively to only one treatment or procedure. With the present inventive single integrated intravascular device, multiple intravascular treatments or procedures may now be carried out in a single streamlined procedure saving time, reducing device exchanges and providing the interventionalist flexibility to permanently deploy a stent scaffold at any point in the thrombectomy procedure. This single integrated intravascular device may be used to carry out multiple intravascular treatments or procedures including clot capture/removal, angioplasty and/or prevention of restenosis.

Figure 1:
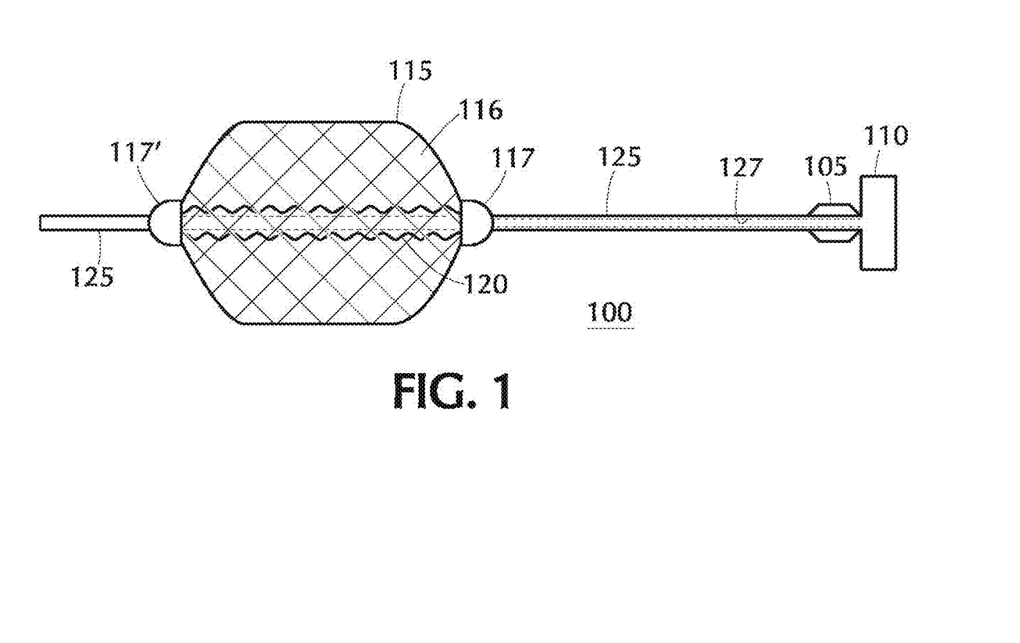
FIG. 1 is a cross-sectional view of an exemplary single integrated intravascular device including a self-expanding stentriever and semi-compliant balloon in accordance with the present invention.

Referring to FIG. 1, the present inventive single integrated intravascular device 100 includes a mechanical thrombectomy device (e.g., self-expanding stentriever) 115 comprising an open mesh, cage, scaffolding, or skeleton formed by a plurality of struts connected together with spaces or openings 116 defined therebetween through which the clot may be engaged, captured and over time embed. Self-expanding stentriever 115 is made of an automatically self-expanding material (e.g., a biocompatible superelastic shape memory material such as Nitinol (e.g., Nickel-Titanium)) that may be crimped-down or reduced in diameter to a compressed state receivable within a lumen of a microcatheter, as described in further detail below. Housed within the self-expanding stentriever 115 is a deflated semi-compliant balloon 120. Proximal and distal ends of each of the semi-compliant balloon 120 and self-expanding stentriever 115 are secured (e.g., fused) at respective proximal and distal securement points 117, 117' to a proximal shaft or pusher member 125. As is illustrated in FIG. 1, a proximal section of the pusher member 125 extends proximally to and axially completely through the semi-compliant balloon 120, while a distal section of the pusher member 125 extends outward beyond the distal end of the semi-compliant balloon 120 and self-expanding stentriever 115.

The stiffness of pusher member 125 preferably varies along its axial length from a stiff proximal end relative to a more pliable distal end extending axially beyond the semi-compliant balloon and self-expanding stentriever. Defined axially through a portion of the proximal section of the pusher member 125 and in fluid communication with the semi-compliant balloon 120 is an inflation/deflation lumen 127 for receiving an inflation media (e.g., 50% contrast saline solution) used to inflate/deflate the semi-compliant balloon 120. As is evident from the illustration in FIG. 1, the inflation/deflation lumen 127 is in fluid communication with the semi-compliant balloon, without extending axially beyond the semi-compliant balloon into the distal section of the pusher member 125.

Heretofore, multifunctional intravascular medical procedures (i.e., clot capture/retrieval; angioplasty; and thereafter implantation of a permanent stent to prevent restenosis) all required different separate medical devices used in successive medical treatments. These separate medical treatments have been streamlined using the present inventive single integrated intravascular device. A general overview of the multifunctional application of the present inventive single integrated intravascular device is provided, the specific details of operating the device follow in the description thereafter. Initially the target clot may be captured using the self-expanding stentriever component of the present inventive single integrated intravascular device and withdrawn into a proximal catheter. Thereafter, imaging may be conducted to determine whether underlying residual stenosis is present at the original site of the target clot. If the presence of underlying residual stenosis is detected at the original site of the target clot, the same single integrated intravascular device 100 may be reloaded into the microcatheter and reintroduced back to the original site of the target clot where the underlying residual stenosis has been detected. At that original site in the vessel angioplasty may be performed on the underlying residual stenosis dilating the opening of the artery to restore blood flow therethrough by inflating the semi-compliant balloon housed within the self-expanding stentriever. With inflation of the semi-compliant balloon the self-expanding stentriever may be detached or released (freed) from the remaining portion of the single integrated intravascular device. The remaining portion of the single integrated intravascular device may thereafter be withdrawn leaving behind permanently in the vessel the detached or released (freed) portion of the self-expanding stentriever while in the self-expanded state to prevent elastic vessel recoil or restenosis.

A detailed description of the use of the single integrated intravascular device follows below. Because the present inventive single integrated intravascular device employs a semi-compliant balloon, prior to introduction into the body the single integrated device is prepped by removing, purging, or exhausting residual air from the device. Removal of the residual air may be achieved by applying a vacuum using a syringe 110 or other mechanical device connected to a proximal hub 105. The exemplary illustration in FIG. 1 shows a single inflation/deflation lumen 127, however, it is contemplated and within the intended scope of the present invention for separate inflation and deflation lumen (arranged coaxially or side-by-side) to be employed, as desired.

Figure 2A:
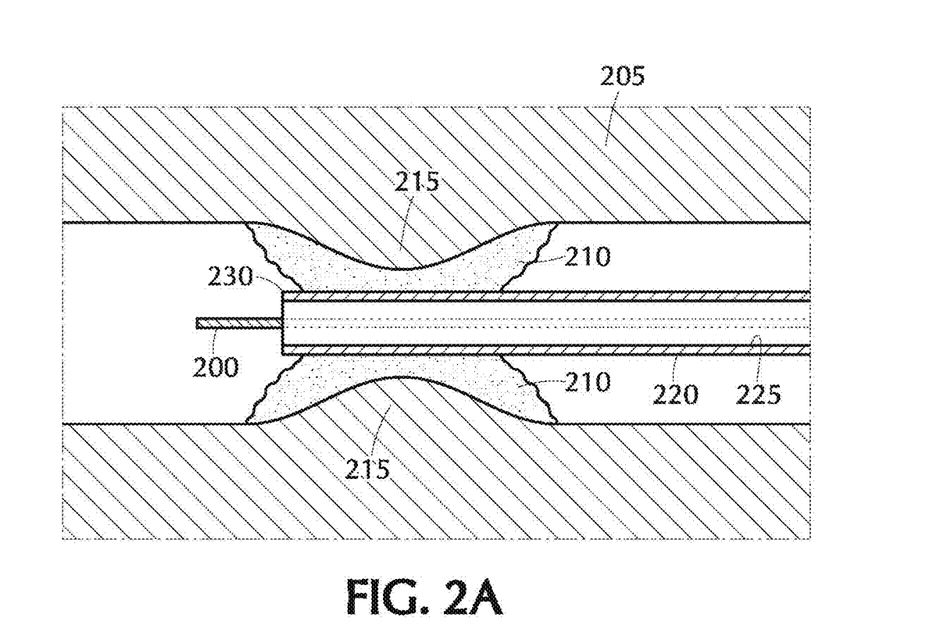
FIG. 2A depicts the guidewire and microcatheter positioned across the target clot in a vessel.
Figure 2B:
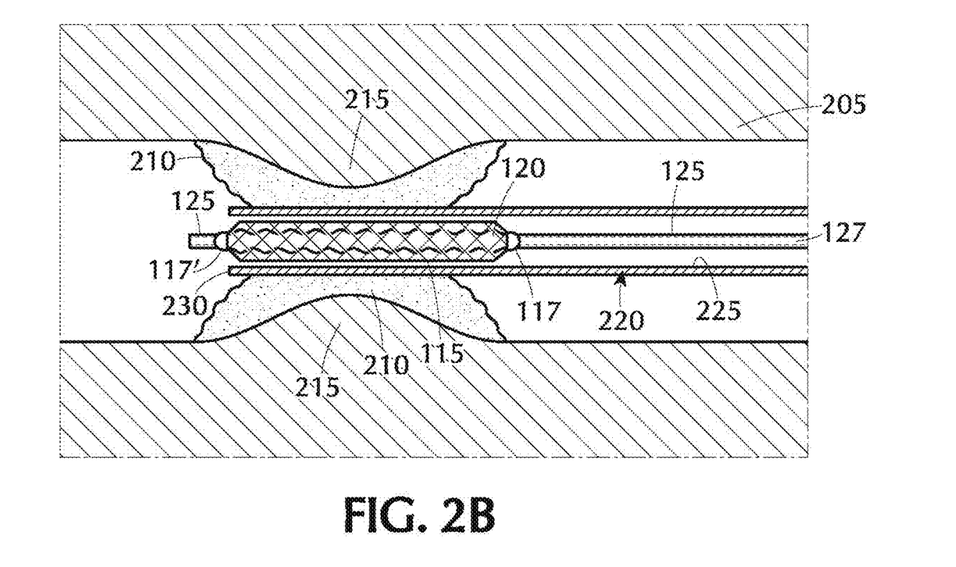
FIG. 2B depicts, following proximal withdrawal of the guidewire from the vessel, advancement through the lumen of the microcatheter the present inventive single integrated intravascular device of FIG. 1 so that the self-expanding stentriever traverses the target clot in the vessel.
Figure 2C:
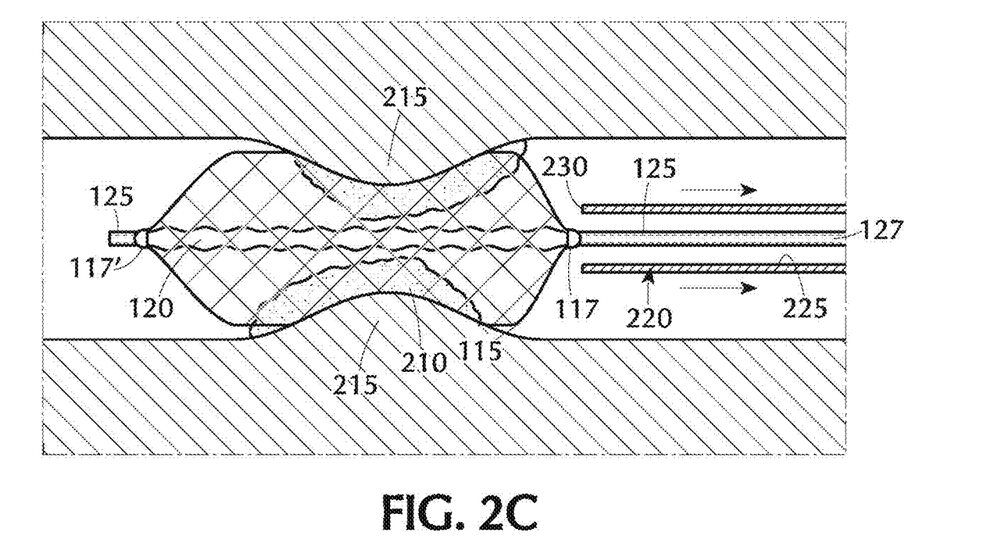
FIG. 2C depicts, following proximal withdrawal of the microcatheter from the vessel, unsheathing and automatic deployment of the self-expanding stentriever to a radially self-expanded state engaging the target clot in the open spaces of the scaffolding.
Figure 2D:
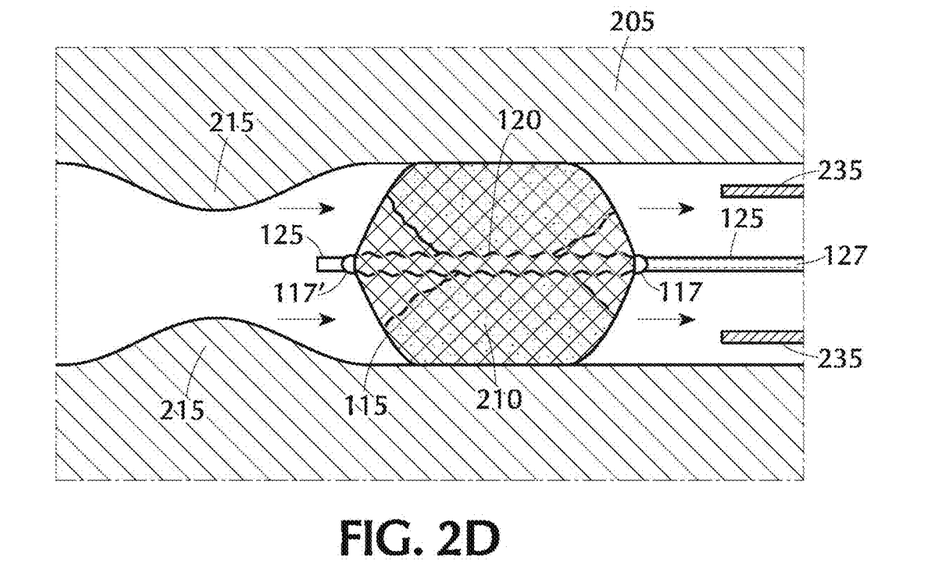
FIG. 2D depicts the self-expanding stentriever while in a radially self-expanded state with the clot embedded therein being withdrawn proximally into a larger diameter proximal catheter.

Once prepped, use of the present inventive single integrated device 100 begins by introducing a guidewire 200 into an artery 205 and advancing the guidewire across the target clot, thrombus, occlusion or blockage 210, as shown in FIG. 2A. Thereafter, a microcatheter 220 having a lumen 225 defined axially therein is tracked over the guidewire 200 until its distal end 230 crosses and emerges distally beyond the target clot 210. Guidewire 200 is then proximally withdrawn from the vessel while maintaining the position of the microcatheter 220 in the vessel 205 traversing the target clot 210. Referring to FIG. 2B, while the self-expanding stentriever 115 is in a compressed state (e.g., sheathed by the microcatheter so as to be crimped-down having a reduced diameter) with the deflated semi-compliant balloon 120 housed therein, the single integrated intravascular device 100 is introduced into the lumen 225 of the microcatheter 220. Guided by imaging, the single integrated intravascular device 100 is advanced through the lumen 225 of the microcatheter 220 using the pusher member 125 so that the self-expanding stentriever 115 traverses the target clot 210. Referring to FIG. 2C, the microcatheter 220 is then retracted or withdrawn proximally while the single integrated intravascular device 100 remains in place within the vessel 205 traversing/crossing the target clot 210. As the microcatheter 220 is proximally retracted from the vessel 205 it unsheathes or frees the self-expanding stentriever 115 disposed therein which automatically transitions to a self-expand state having an enlarged diameter thereby engaging the target clot 210 in the open spaces 116 of the mesh or scaffolding structure. While the scaffolding or skeleton structure of the self-expanding stentriever 115 expands radially outward, the semi-compliant balloon 120 housed therein remains in a deflated state so as not to interfere with engagement and subsequent embedding of the target clot 210. Over time (e.g., approximately 2-5 minutes) the target clot 210 sufficiently embeds in the spacings or openings 116 of the scaffolding of the self-expanding stentriever 115. Thereafter, the target clot 210 embedded in the self-expanding stentriever 115 together with the deflated semi-compliant balloon 120 housed therein are withdrawn proximally as a single unit and received in a proximal catheter 235 having a diameter sufficiently large in size to accommodate the self-expanding stentriever 115 (which in a self-expanded state) without compressing and stripping off the target clot, as depicted in FIG. 2D.

The functionality of the present inventive single integrated intravascular device does not necessarily end. Now that the self-expanding stentriever 115 and captured target clot 210 therein have been received in the proximal catheter 235 and withdrawn from the vessel 205, the presence of any underlying residual stenosis 215 at the original site of the captured target clot may be detected through imaging.

Figure 2E:
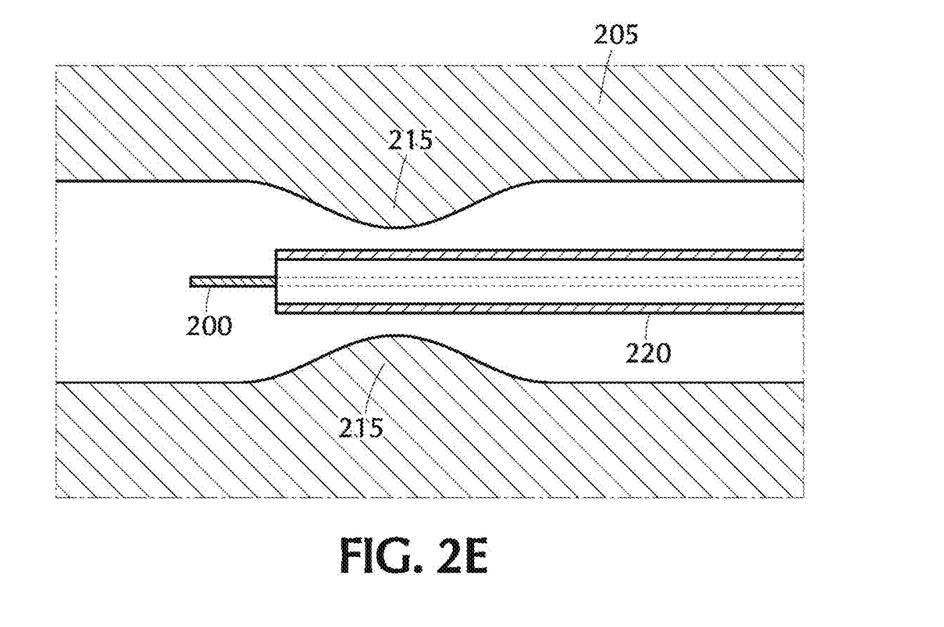
FIG. 2E depicts the presence of an underlying residual stenosis at the original site in the vessel of the target clot, the guidewire and microcatheter being reintroduced, simultaneously or in succession, into the vessel to a position coinciding with the underlying residual stenosis.
Figure 2F:
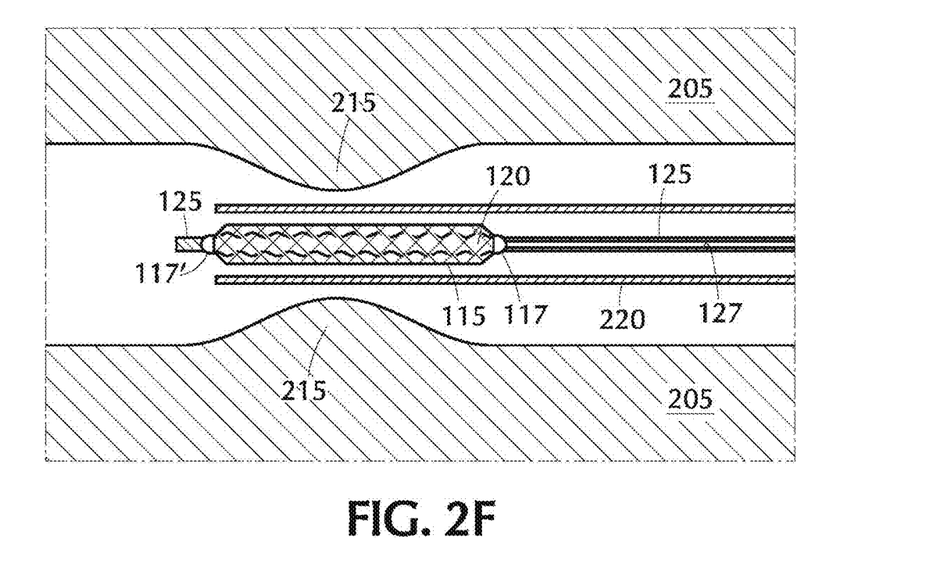
FIG. 2F depicts, following proximal withdrawal of the guidewire from the vessel, reloading of the present inventive single integrated intravascular device of FIG. 1 into the lumen of the microcatheter so that the self-expanding stentriever coincides with the underlying residual stenosis.
Figure 2G:
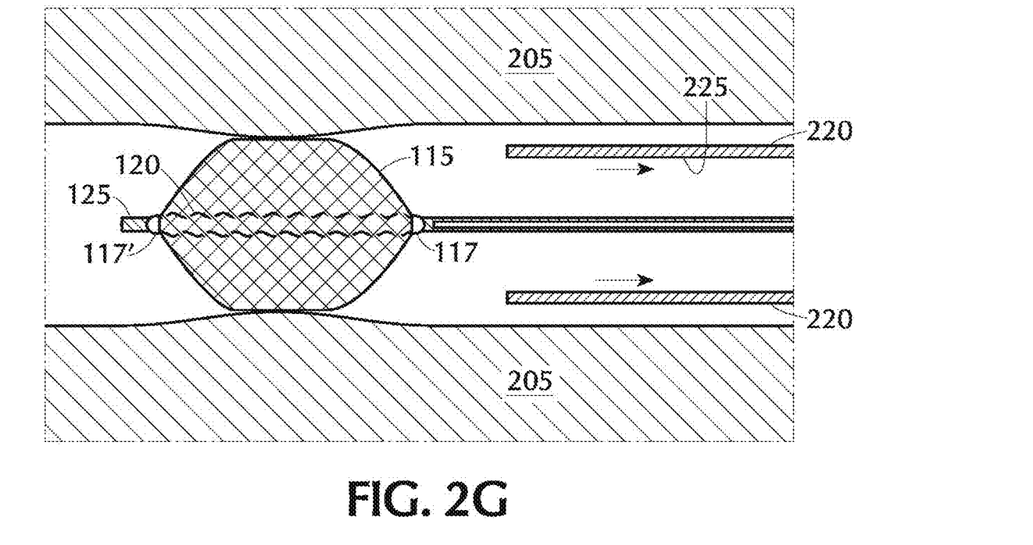
FIG. 2G depicts, following proximal withdrawal of the microcatheter from the vessel, unsheathing and automatic deployment of the self-expanding stentriever to a radially self-expanded state at the location of the detected underlying residual stenosis.

If residual stenosis 215 is detected during imaging, the single integrated intravascular device 100 may be cleaned and reloaded into the microcatheter 220. Similar to that in FIG. 2A (but the target clot 210 has already been captured and removed from the vessel), the guidewire 200 and microcatheter 220, either successively (one after the other) or simultaneously at the same time, are reintroduced and tracked through the vessel 205 to the detected underlying residual stenosis 215, as illustrated in FIG. 2E. Guidewire 200 is then proximally withdrawn from the vessel leaving the microcatheter 220 in position coinciding with the underlying residual stenosis 215. While the self-expanding stentriever 115 is in the compressed state (i.e., crimped-down having a reduced diameter) with the deflated semi-compliant balloon 120 housed therein, the single integrated intravascular device 100 is reloaded into the microcatheter 220 and advanced so that the self-expanding stentriever 115 coincides with the underlying residual stenosis 215, as shown in FIG. 2F. Referring to FIG. 2G, microcatheter 220 is withdrawn proximally from the vessel 205 unsheathing the self-expanding stentriever 115 allowing it to automatically enlarge radially to the self-expanded state. With the self-expanding stentriever 115 in the self-expanded state, the syringe 110 dispenses under pressure the inflation media through the inflation lumen 127 of the pusher member 125 filling the semi-compliant balloon 120. Self-expanding stentriever 115 may be configured so that some portions of the scaffolding or struts include weakened or frangible sections 111 disposed at multiple strut locations proximate the proximal and distal securement points to the pusher member 125. The frangible sections 111 of the self-expanding stentriever may be designed as sections of the struts having a thinner cross-section (as depicted in FIG. 2J), or as struts with focal stress risers (notches).

Figure 2H:
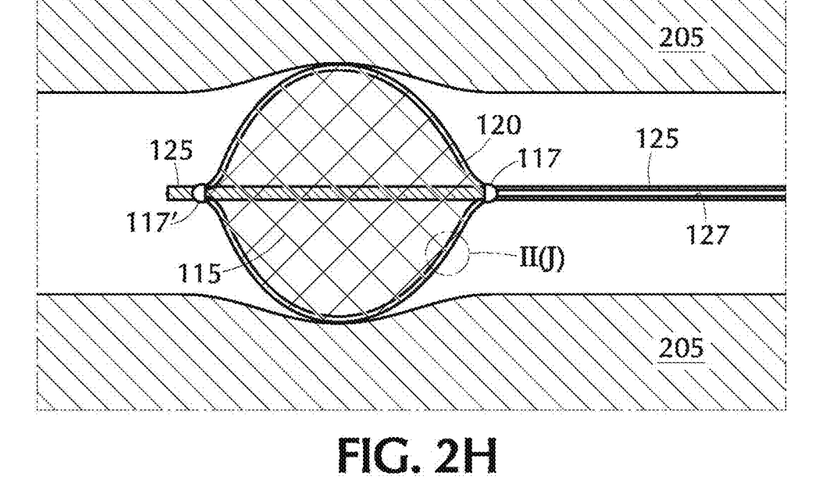
FIG. 2H depicts, inflation of the semi-compliant balloon housed within the self-expanding stentriever, to dilate the vessel at the detected underlying residual stenosis; the self-expanding stentriever is illustrated in a hyper-expanded state larger in diameter than that when in the self-expanded state of FIG. 2G.

As the semi-compliant balloon 120 inflates imposing a radially outward force, the self-expanding stentriever 115 hyper-expands to a diameter larger than the self-expanding state while adopting the curved contour of the inflated semi-compliant balloon, as shown in FIG. 2H. The inflated balloon enlarges or dilates the narrow opening of the vessel in which there is a build-up of plaque improving blood flow therethrough.

Figure 2I:
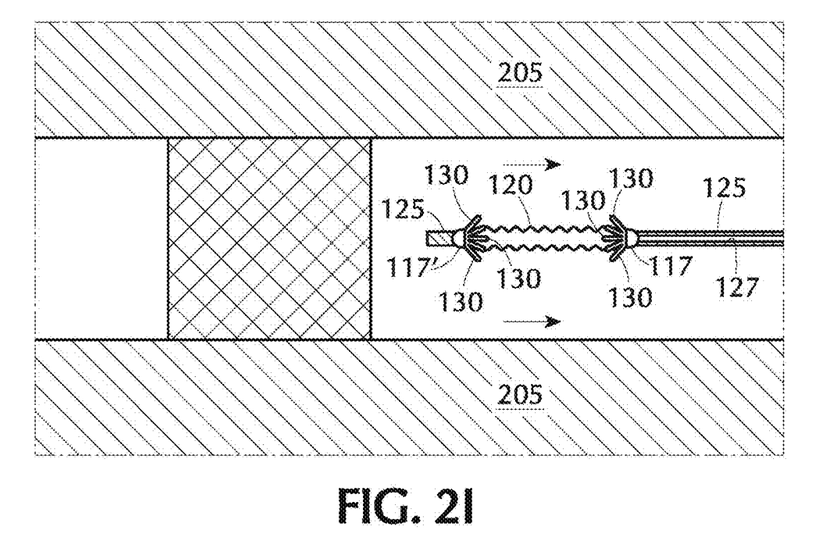
FIG. 2I depicts, following fracture of the frangible sections of the scaffolding of the self-expanding stentriever when deformed by the inflated semi-compliant balloon and thereafter deflating of the semi-compliant balloon, proximal withdraw from the vessel as a single unit the remnant portions of the self-expanding stentriever that remain secured to the pusher shaft along with the deflated balloon, while permanently maintaining in position within the vessel the detachable portion of the self-expanding stentriever in the self-expanded state to prevent restenosis.
Figure 2J:
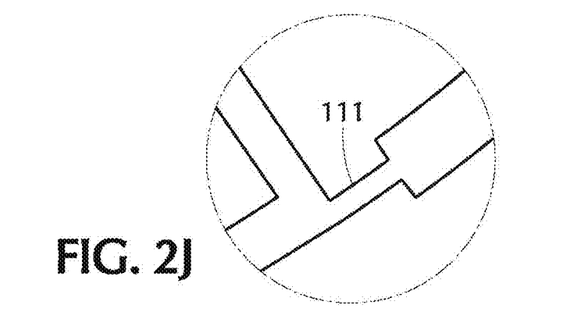
FIG. 2J is an enlarged area of a section II(J) of struts of the self-expanding stentriever in FIG. 2H having a thinner cross-section to promote fracturing when the semi-compliant balloon is inflated causing the self-expanding stentriever to transition to a hyper-expanded state.

At some point during inflation of the semi-compliant balloon 120, sufficient radially outward force is imposed to deform the frangible sections 111 of the self-expanding stentriever 115 causing the frangible sections 111 to fracture or break. Fracturing of the frangible sections 111 completely frees or releases a detachable portion 130' of self-expanding stentriever 115 from that that of remnant portions 130 of the self-expanding stentriever 115 that remain secured to the pusher member 125 at respective proximal and distal securement points. A negative pressure is applied using the syringe 110 expelling the inflation media via the inflation/deflation lumen 127 of the pusher member 125 so that the collapsed semi-compliant balloon 120 may be withdrawn from the vessel. As the semi-compliant balloon 120 collapses, the detachable portion 130' of the self-expanding stentriever transitions from the hyper-expanded state (FIG. 2H) back to the smaller diameter self-expanded state (FIG. 2I). FIG. 2I further depicts the severed detachable portion 130' of the self-expanding stentriever maintained in the vessel 205 in the self-expanded state, while the remnant portions 130 secured to the pusher member 125 together with the deflated semi-compliant balloon 120 are proximally withdrawn from the vessel as a single unit. Detachable portion 130' of the self-expanding stentriever 115 in the self-expanded state remains permanently in the vessel at the position in which residual stenosis was detected to prevent restenosis. Accordingly, the probability of restenosis (re-narrowing of the opening of the artery) that occurs (typically within approximately 6-12 months) following dilation of the vessel opening by the inflated balloon is prevented or reduced by the detachable portion of the self-expanding stentriever permanently remaining in place in the vessel.

Figure 3A:
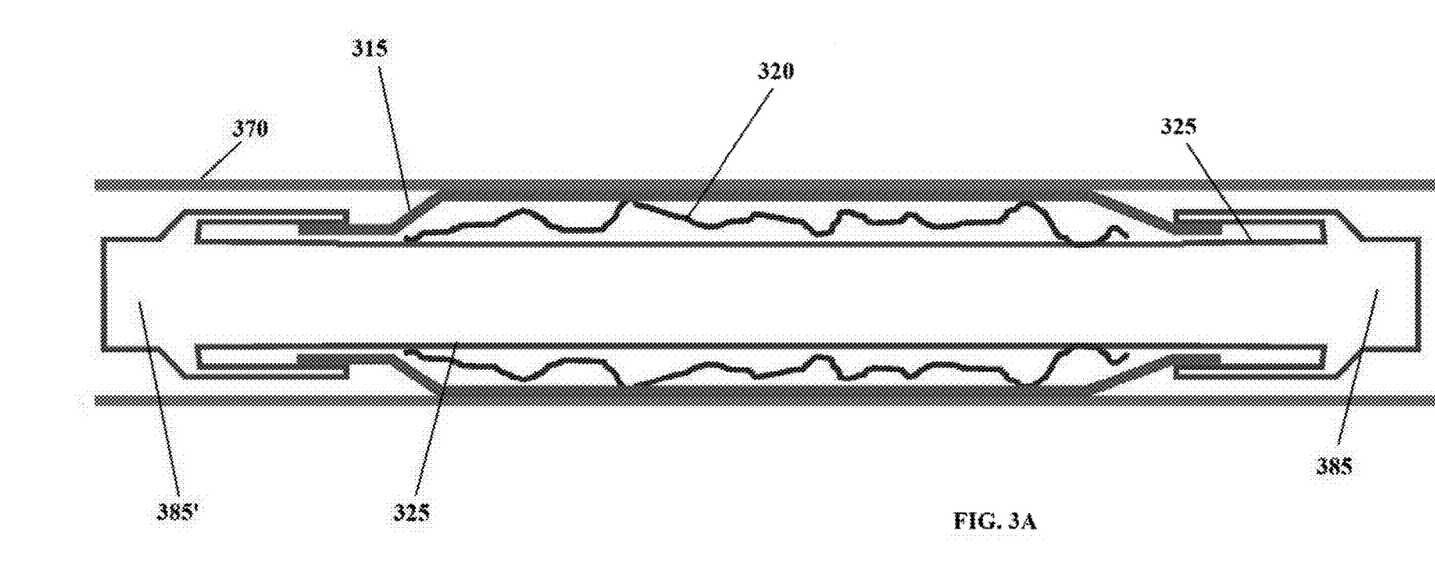
FIG. 3A is a cross-sectional view of an alternative configuration of the present inventive single integrated intravascular device including a self-expanding stentriever and semi-compliant balloon in accordance with the present invention; wherein distal and proximal ends of the self-expanding stentriever are releasably secured to the pusher member via respective distal and proximal sleeves.
Figure 3B:
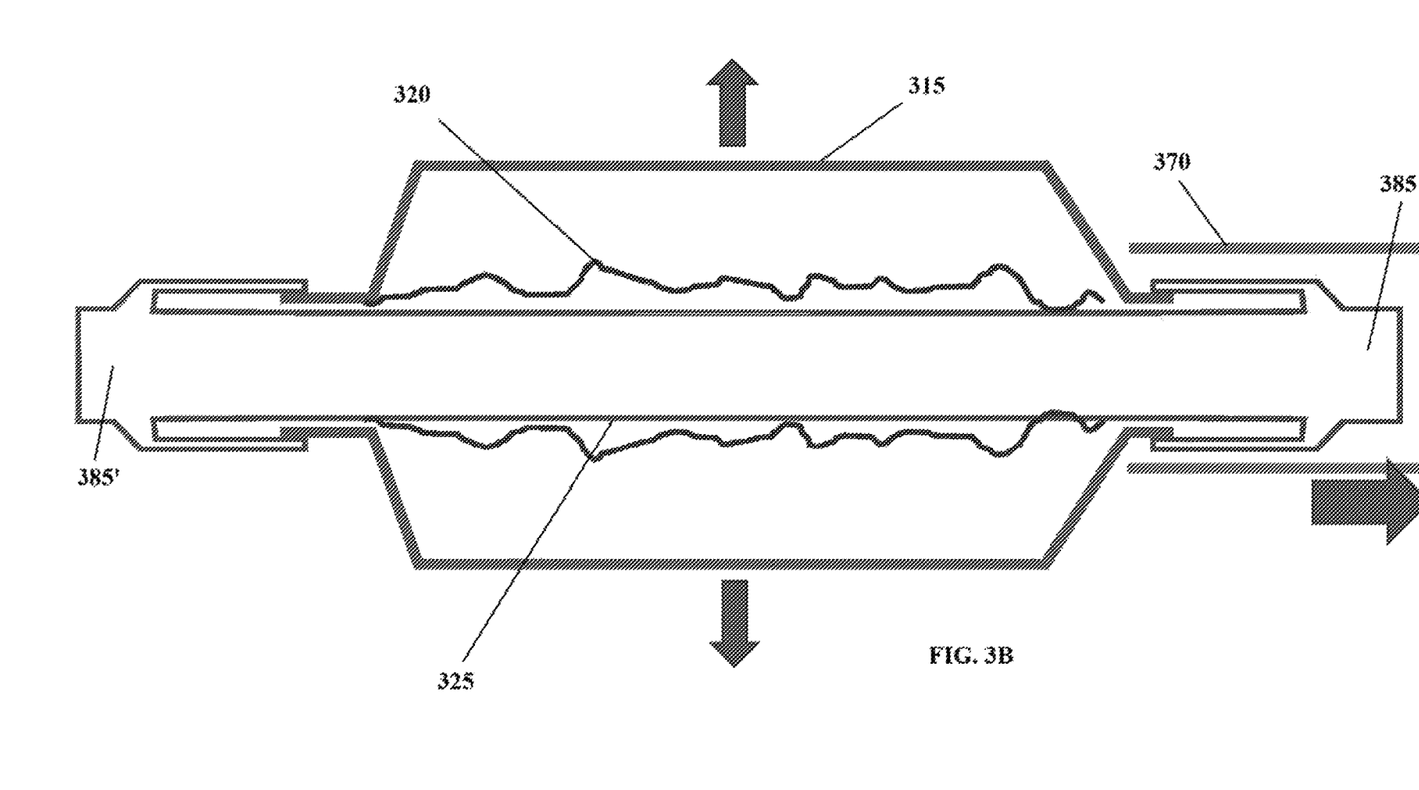
FIG. 3B is a cross-sectional view of the single integrated intravascular device of FIG. 3A after the self-expanding stentriever has been unsheathed from the microcatheter and transitioning to the self-expanded state.
Figure 3C:
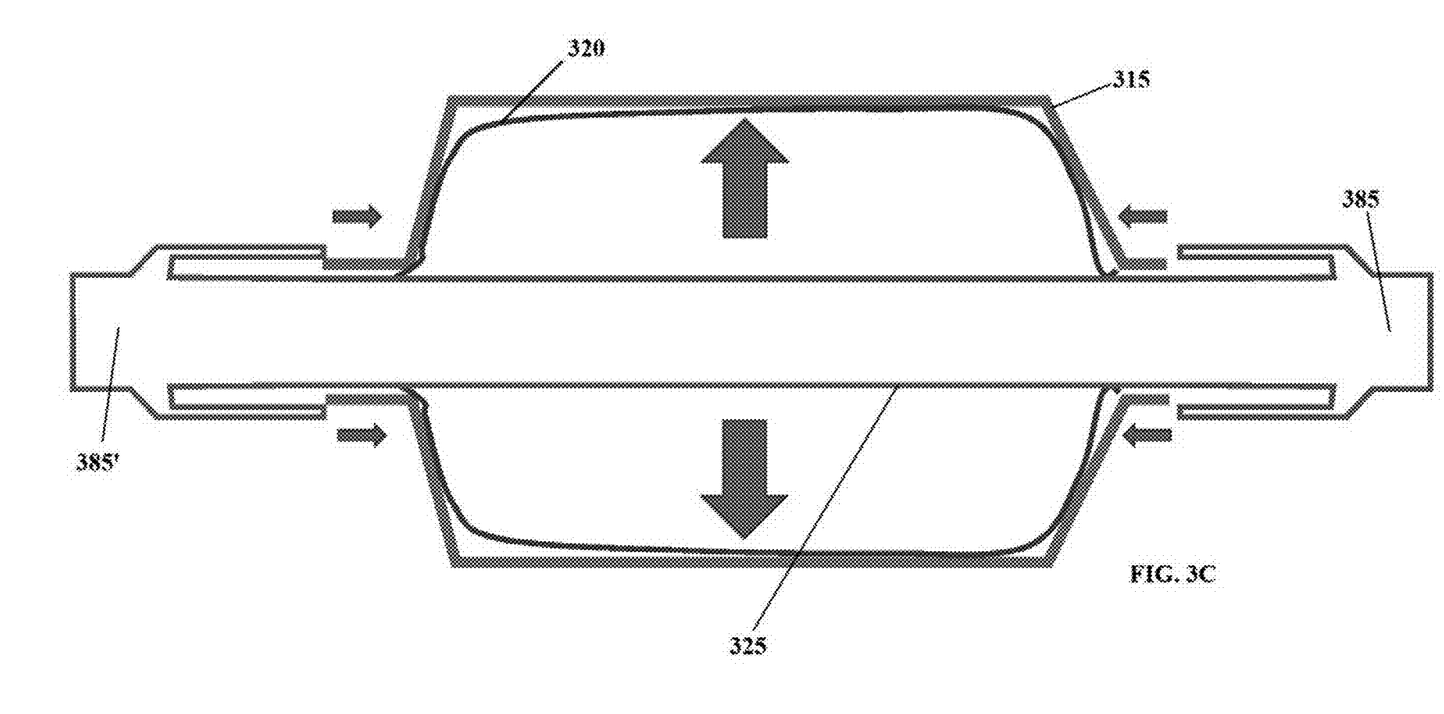
FIG. 3C is a cross-sectional view of the single integrated intravascular device of FIG. 3A when the semi-compliant balloon has been inflated resulting in radial expansion of the self-expanding stentriever to a hyper-expanded state (having a greater diameter than the self-expanded state in FIG. 3B) simultaneously with a foreshortening axially of the respective proximal and distal ends of the self-expanding stentriever.
Figure 3D:
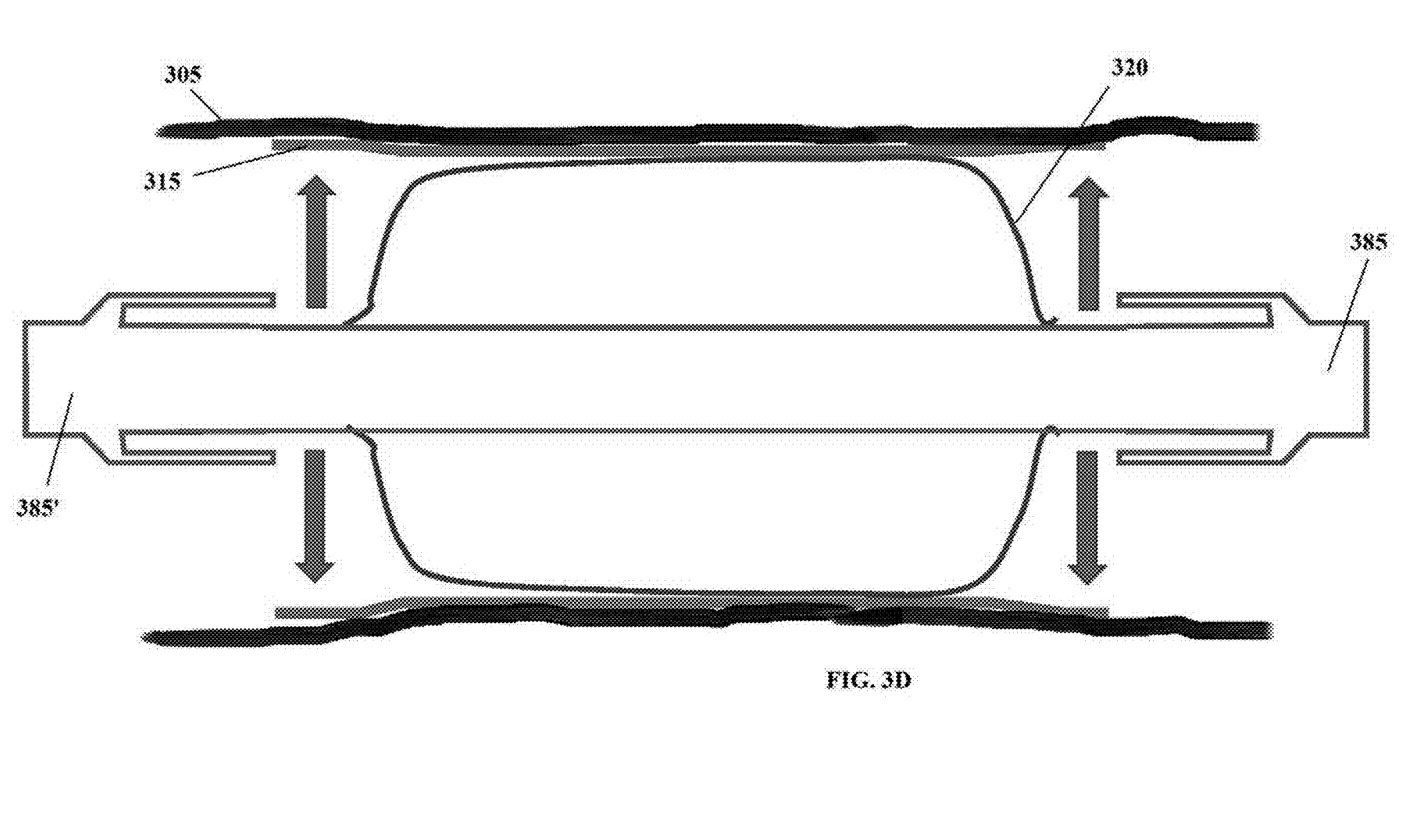
FIG. 3D is a cross-sectional view of the single integrated intravascular device of FIG. 3A with the proximal and distal ends of self-expanding stentriever released or disengaged from the respective proximal and distal sleeves allowing the released self-expanded stentriever to return to its pre-formed shape.

Instead of designing the struts of the self-expanding stentriever to have frangible sections 111 that break or fracture when deformed, the self-expanding stentriever may alternatively be releasably secured to the pusher member. By way of illustrative example, FIG. 3A depicts an alternative configuration, wherein the self-expanding stentriever 315 (while in a crimped state) with the deflated semi-compliant balloon 320 disposed therein together are advanced through the microcatheter 370 to a target site in the vessel. Proximal and distal end struts of the self-expanding stentriever 315 are secured to the pusher member 325 via proximal and distal sleeves or end caps 385, 385', respectively, that remain fixed in position axially relative to one another. When the microcatheter 370 is withdrawn proximally, the self-expanding stentriever 315 no longer constrained by the microcatheter automatically self-expands increasing in diameter to a self-expanded state, as shown in FIG. 3B. Despite such expansion, the distal and proximal end struts of the self-expanding stentriever 315 nevertheless remain constrained or secured by the proximal and distal sleeves 385, 385'. Thus, the self-expanding stentriever 315 while in the self-expanded state may be employed similar to that described above with respect to FIGS. 2A-2J to engage and remove the target clot. If, subsequent to removing the target clot, through imaging a stenosis is detected at the site of the removed target clot, the device may be cleaned and reloaded into the vessel to the target site, once again following the description and procedure above regarding the design of FIGS. 2A-2J. Once the self-expanding stentriever is positioned at the target site the microcatheter 370 is proximally withdrawn. The unsheathing of the crimped-down self-expanding stentriever 315 increases its diameter to a self-expanded state, nevertheless the distal and proximal end struts of the self-expanding stentriever remain secured to the pusher member 325 beneath the respective proximal and distal sleeves 385, 385'. Referring to FIG. 3C, the semi-compliant balloon 320 is inflated causing the self-expanding stentriever 315 to transition to a hyper-expanded state (i.e., having a diameter greater than that in a self-expanded state when the self-expanding stentriever is unsheathed by the microcatheter but remains secured by the proximal and distal sleeves 385, 385', as shown in FIG. 3B). Inflation of semi-compliant balloon 320 to the hyper-expanded state, increases in diameter (direction traverse to the axial direction—as denoted by the larger arrows) and, in turn, causes a foreshortening of the self-expanding stentriever (axial direction—as denoted by the smaller arrows drawn towards one another) to such extent that the distal and proximal end struts of the self-expanding stentriever are freed from or disengage (no longer secured by) the proximal and distal sleeves 385, 385'. Once released or detached from the proximal and distal sleeves (as shown in FIG. 3D), the distal and proximal end struts of the self-expanding stentriever expand automatically in diameter to their pre-formed shape in direct physical contact with the inner wall of the vessel at the target site of the stenosis. Thereafter, semi-compliant balloon 320 may be deflated and removed proximally along with the sleeves 385, 385' and pusher member 325, while the detached (freed) self-expanding stentriever 315 permanently remains in physical contact with the inner wall of the vessel 305 at the target site.

Regardless of the particular design or configuration of the device, if the self-expanding stentriever is substantially "waisted" indicating an inability to embed into the target clot while the presence of an underlying stenosis is probable, the step of removing the target clot may be bypassed entirely. In such case, the interventionalist may proceed directly to inflating the semi-compliant balloon causing the self-expanding stentriever to transition to a hyper-expanded state and detaching/releasing itself from the pusher member, without attempting to remove or withdraw the clot. After deflation, the semi-compliant balloon is withdrawn together with the pusher member, leaving in place at the site of the stenosis the detached/released self-expanding stentriever in the self-expanded state in physical contact against the wall of the vessel.

Thus, the present inventive single integrated intravascular device is used to perform multifunctional treatment including: (i) capturing and removing the target clot; (ii) dilating the narrowed opening of a vessel in which an underlying residual stenosis is detected beneath the target clot after removal; and/or (iii) permanently maintaining the detachable/releasable (freed) self-expanding stentriever in the vessel at the location of the detected underlying residual stenosis to prevent restenosis.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A single integrated intravascular device, comprising:
   a pusher member having a proximal end, an opposite distal end;
   a self-expanding stentriever comprising an open scaffolding formed by multiple struts secured together; the self-expanding stentriever being transitionable upon withdraw of an externally applied mechanical force between a compressed state having a reduced diameter and a self-expanded state having an enlarged diameter; proximal and distal ends of the self-expanding stentriever being secured to the pusher member at respective proximal and distal securement points; the self-expanding stentriever being detachable or releasable from the pusher member at the respective proximal and distal securement points;
   a semi-compliant balloon housed within the self-expanding stentriever and secured to the pusher member extending axially through the semi-compliant balloon; and
   an inflation lumen defined axially in the pusher member in fluid communication with the semi-compliant balloon;
   wherein the proximal and distal ends of the self-expanding stentriever are releasably securable to the pusher member via respective proximal and distal sleeves;
   wherein the proximal and distal ends of the self-expanding stentriever are releasable from the respective proximal and distal sleeves only when the semi-compliant balloon is inflated and the self-expanding stentriever is in a hyper-expanded state having a larger diameter than while in the self-expanded state.

2. A method for using a single integrated intravascular device including: a pusher member having a proximal end, an opposite distal end; a self-expanding stentriever comprising an open scaffolding formed by multiple struts secured together; the self-expanding stentriever transitionable upon withdraw of an external mechanical force between a compressed state having a reduced diameter and a self-expanded state having an enlarged diameter; proximal and distal ends of the self-expanding stentriever being secured to the pusher member at respective proximal and distal securement points; the self-expanding stentriever being detachable or releasable at the respective proximal and distal securement points; a semi-compliant balloon housed within the self-expanding stentriever and secured to the pusher member extending axially through the semi-compliant balloon;
   and an inflation lumen defined axially in the pusher member in fluid communication with the semi-compliant balloon; the method comprising the steps of:
   advancing a guidewire and microcatheter into a vessel across a target clot;
   proximally withdrawing the guidewire while maintaining in position the microcatheter in the vessel traversing the target clot;
   while the self-expanding stentriever is in the compressed state with the semi-compliant balloon in a deflated state housed therein, loading the single integrated intravascular device into the lumen of the microcatheter;
   advancing the single integrated intravascular device through the lumen of the microcatheter using the pusher member so that the self-expanding stentriever coincides with the target clot;
   proximally withdrawing from the vessel the microcatheter, while the single integrated intravascular device is maintained within the vessel crossing the target clot; the self-expanding stentriever when unsheathed from the microcatheter automatically transitioning to the self-expanded state engaging the target clot in the open scaffolding of the self-expanding stentriever, while the semi-compliant balloon housed within the self-expanding stentriever is maintained in a deflated state so as not to interfere with engagement and subsequent embedding of the target clot in the self-expanding stentriever.

3. The method according to claim 2, further comprising the steps of:
  proximally withdrawing from the vessel as a single unit receivable in a proximal catheter the target clot embedded in the self-expanding stentriever while in the self-expanded state together with the semi-compliant balloon while in the deflated state housed therein;
  detecting through imaging the presence of an underlying residual stenosis at an original site of the captured target clot in the vessel;
  advancing the guidewire and microcatheter back into the vessel coinciding with the detected underlying residual stenosis;
  proximally withdrawing from the vessel the guidewire while maintaining in position the microcatheter in the vessel coinciding with the underlying residual stenosis;
  while the self-expanding stentriever is in the compressed state with the semi-compliant balloon in the deflated state housed therein, reloading the single integrated intravascular device into the lumen of the microcatheter;
  advancing the single integrated intravascular device through the lumen of the microcatheter using the pusher member so that the self-expanding stentriever coincides with the detected underlying residual stenosis;
  proximally withdrawing from the vessel the microcatheter while the single integrated intravascular device is maintained within the vessel coinciding with the detected underlying residual stenosis; the self-expanding stentriever when unsheathed by the microcatheter automatically transitioning to the self-expanded state;
  while the self-expanding stentriever is in the self-expanded state, dispensing under pressure inflation media through the inflation lumen of the pusher member inflating the semi-compliant balloon;
  as the balloon inflates imposing radially outward force, transitioning the self-expanding stentriever from the self-expanded state to a hyper expanded state thereby dilating the vessel at the detected underlying residual stenosis while releasing or detaching the self-expanding stentriever from the pusher member.

4. The method according to claim 3, wherein the releasing or detaching of the self-expanding stentriever from the pusher member comprises the step of:
  as the semi-compliant balloon is inflated expanding radially outward the self-expanding stentriever to a hyper-expanded state, fracturing frangible sections of some of the multiple struts of the self-expanding stentriever disposed proximate the respective proximal and distal securement points so as to completely sever a detachable portion of the self-expanding stentriever free of the pusher member from that of remnant portions of the stentriever that remain secured to the pusher member at the respective proximal and distal securement points.

5. The method according to claim 3, wherein the releasing or detaching of the self-expanding stentriever from the pusher member comprises the step of:
  as the semi-compliant balloon is inflated, expanding radially outward the self-expanding stentriever to a hyper-expanded state and, in turn, foreshortening the distal and proximal ends of the self-expanding stentriever until freed from respective proximal and distal sleeves releasably securing the distal and proximal ends of the self-expanding stentriever to the pusher member.

6. The method according to claim 5, wherein the proximal and distal ends of the self-expanding stentriever are releasable from the respective proximal and distal sleeves only when the semi-compliant balloon is inflated and the self-expanding stentriever is in the hyper-expanded state having a larger diameter than while in the self-expanded state.

7. The method according to claim 3, further comprising the step of: collapsing the semi-compliant balloon by applying a negative pressure via the inflation lumen of the pusher member to expel the inflation media; wherein as the semi-compliant balloon collapses, the stentriever automatically transitioning from the hyper-expanded state back to the self-expanded state; and
  while in the self-expanded state, maintaining the released or detached self-expanding stentriever in the vessel coinciding with the detected underlying residual stenosis; and proximally withdrawing from the vessel as a single unit the collapsed semi-compliant balloon and the pusher member.

8. The method according to claim 3, wherein the step of advancing the guidewire and microcatheter back into the vessel coinciding with the detected underlying residual stenosis comprises the step of advancing the guidewire and microcatheter, successively or simultaneously, into the vessel to coincide with the detected underlying residual stenosis.

9. The method according to claim 2, wherein the step of advancing the guidewire and microcatheter into the vessel across the target clot comprises the step of advancing the guidewire and microcatheter, successively or simultaneously, into the vessel and across the target clot.

10. The method according to claim 2, further comprising the steps of:
  while the self-expanding stentriever is in the self-expanded state, dispensing under pressure inflation media through the inflation lumen of the pusher member inflating the semi-compliant balloon;
  as the balloon inflates imposing radially outward force, transitioning the self-expanding stentriever from the self-expanded state to a hyper-expanded state thereby dilating the vessel at the detected underlying residual stenosis while releasing or detaching the self-expanding stentriever from the pusher member.

11. The method according to claim 10, wherein the releasing or detaching of the self-expanding stentriever from the pusher member comprises the step of:
  as the semi-compliant balloon is inflated expanding radially outward the self-expanding stentriever to the hyper-expanded state, fracturing frangible sections of some of the multiple struts of the self-expanding stentriever disposed proximate the respective proximal and distal securement points so as to completely sever a detachable portion of the self-expanding stentriever free of the pusher member from that of remnant portions of the stentriever that remain secured to the pusher member at the respective proximal and distal securement points.

12. The method according to claim 10, wherein the releasing or detaching of the self-expanding stentriever from the pusher member comprises the step of:
  as the semi-compliant balloon is inflated, expanding radially outward the self-expanding stentriever to the hyper-expanded state and, in turn, foreshortening the distal and proximal ends of the self-expanding stentriever until freed from respective proximal and distal sleeves releasably securing the distal and proximal ends of the self-expanding stentriever to the pusher member.

13. The method according to claim 12, wherein the proximal and distal ends of the self-expanding stentriever are releasable from the respective proximal and distal sleeves only when the semi-compliant balloon is inflated and the self-expanding stentriever is in the hyper-expanded state having a larger diameter than while in the self-expanded state.

14. The method according to claim 10, further comprising the steps of:
   collapsing the semi-compliant balloon by applying a negative pressure via the inflation lumen of the pusher member to expel the inflation media; wherein as the semi-compliant balloon collapses, the stentriever automatically transitioning from the hyper-expanded state back to the self-expanded state; and
   while in the self-expanded state, maintaining the released or detached self-expanding stentriever in the vessel at a position coinciding with the detected underlying residual stenosis, and proximally withdrawing from the vessel as a single unit the collapsed semi-compliant balloon and the pusher member.

15. A method for using a single integrated intravascular device including a stentriever and semi-compliant balloon housed within the stentriever, the method comprising the steps of:
   introducing the single integrated intravascular device into a vessel to traverse a target clot;
   deploying the stentriever to a self-expanded state and embedding of the target clot therein;
   removing from the vessel the single integrated intravascular device with the embedded clot therein;
   detecting through imaging an underlying residual stenosis in the vessel at an original position of the captured target clot;
   reintroducing the single integrated intravascular device into the vessel to a location where the stentriever coincides with the detected underlying residual stenosis;
   deploying the stentriever so that it transitions from a compressed state to a self-expanded state;
   inflating the semi-compliant balloon with inflation media to enlarge the stentriever to a hyper-expanded state having a diameter larger than the self-expanded state thereby dilating the vessel at the location of the detected underlying residual stenosis while simultaneously completely detaching or releasing the stentriever from a remaining portion of the single integrated intravascular device;
   collapsing the semi-compliant balloon by purging the inflation media therefrom; and
   proximally withdrawing from the vessel the remaining portion of the single integral intravascular device, while maintaining in position within the vessel at the position of the detected underlying residual stenosis the detachable or releasable portion of the stentriever in the self-expanded state.

* * * * *